(12) United States Patent
Gaal et al.

(10) Patent No.: US 6,375,349 B1
(45) Date of Patent: Apr. 23, 2002

(54) INSTRUMENT CONFIGURED TO TEST MULTIPLE SAMPLES FOR THE DETERMINATION OF THERMOPHYSICAL PROPERTIES BY THE FLASH METHOD

(75) Inventors: Peter S. Gaal; Silviu P. Apostolescu, both of Monroeville, PA (US)

(73) Assignee: Anter Corporation, Pittsburgh, PA (US)

(*) Notice: Subject to any disclaimer, the term of this patent is extended or adjusted under 35 U.S.C. 154(b) by 0 days.

(21) Appl. No.: 09/368,554

(22) Filed: Aug. 5, 1999

(51) Int. Cl.$^7$ .................. G01N 25/16; G01N 25/18; G01N 25/20
(52) U.S. Cl. ............... 374/44; 374/43; 374/45; 374/12; 374/56; 374/179
(58) Field of Search ................... 374/43, 44, 12, 374/45, 55, 56, 179

(56) References Cited

U.S. PATENT DOCUMENTS

| | | | | |
|---|---|---|---|---|
| 3,165,915 A | * | 1/1965 | Parker et al. | 374/44 |
| 4,381,154 A | * | 4/1983 | Hammond III | 374/43 |
| 4,874,250 A | * | 10/1989 | Gonner | 374/43 |
| 4,928,254 A | | 5/1990 | Knudsen et al. | 702/136 |

FOREIGN PATENT DOCUMENTS

| | | | | |
|---|---|---|---|---|
| DE | 4301987 A1 | * | 7/1994 | 374/43 |

OTHER PUBLICATIONS

Soelter, H., PTO 2001–3698, STIC Translation (Jul. 2001) of DE 43 01 987 A1, 24 Pages, Jul. 1994.*
Thermitus, M.-A., and Gaal, P.S., "Specific Heat Measurement in a multisample environment with the laser flash method," Thermal Conductivity 24 / Thermal Expansion 12, pp. 219–228 (Jan. 11, 1999).*
Parker et al., "Flash Method of Determining Thermal Diffusivity, Heat Capacity, and Thermal Conductivity." J. Appl. Phys., 32(9):1679–1684, (1961).*
Muraybayashi et al., "Measurement of Heat Capacity at High Temperatures by Laser Flash Method—Heat Capacity of Alumina", Journal of Nuclear Science and Technology, 7(6): 312–316 (Jun. 1970).*
Rudkin, R.L., Jenkins, R.J., and Parker, W.J., "Thermal Diffusivity Measurements on Metals at High Temperatures," The Review of Scientific Instruments, 33(1): 21–24 (Jan. 1962).*

* cited by examiner

Primary Examiner—Christopher W. Fulton
Assistant Examiner—Stan Pruchnic
(74) Attorney, Agent, or Firm—Richard D. Fuerle

(57) ABSTRACT

An instrument for determining thermophysical properties of a solid sample of uniform thickness is disclosed. The instrument comprises a furnace, an elliptical mirror outside the furnace, a light source at one focus of the elliptical mirror that is closest to the elliptical mirror, a beam guide having one end at the other focus of the elliptical mirror and the other end inside the furnace, a sample holder inside the furnace capable of holding at least two diffusivity samples with the front and back surface of a sample exposed, an indexing system for moving the sample holder so as to place samples held by the sample holder in the path of light leaving the beam guide, and an infrared detector for quantifying changes in the temperature of the back surface of a sample that is in the path of the light. Methods for determining the thermal diffusivity, specific heat capacity, thermal conductivity, coefficient of thermal expansion, density, and temperature of a sample using this instrument are also disclosed.

26 Claims, 4 Drawing Sheets

INSTRUMENT CONFIGURED TO TEST MULTIPLE SAMPLES FOR THE DETERMINATION OF THERMOPHYSICAL PROPERTIES BY THE FLASH METHOD

BACKGROUND OF THE INVENTION

This invention relates to an instrument and to the use of that instrument to determine certain thermophysical properties of solid samples. In particular, it relates to an instrument having an elliptical mirror, a light source at one focus, and a beam guide at the other focus, where the beam guide conducts light into a furnace containing the samples to be analyzed.

Thermal diffusivity is the speed that heat travels through a material. In the flash method of measuring thermal diffusivity, an energy pulse is deposited on the front face of a slab of uniform thickness and the resulting temperature rise on the back face is recorded as a function of time. By assuming a slab of homogenous solid material and a uniformly distributed, infinitesimally short duration energy pulse, Parker, et al. (*J.Appl. Phys.*, 32(9): 1679–1684, 1961) were able to derive the thermal diffusivity, $\alpha$, from that temperature time relationship using the equation $$a = \frac{0.138 d^2}{\pi^2 t_{\frac{1}{2}}}$$

where d is the thickness of the slab (in millimeters) and $t_{1/2}$ is the time (in seconds) required for the temperature of the back face to reach one half of its maximum value (the "half-max time"). The simple elegance of this relationship has made the method very popular and instruments based on it are commercially available.

Since thermal diffusivity can now be more easily determined, it is also easier to determine other thermal properties that are related to it through the fundamental equation K=$\alpha\rho$Cp, K is the thermal conductivity (W/mK), Cp is the specific heat capacity (joules/kgK), and $\rho$ is bulk density (kg/m$^3$). Both Cp and K are very important in design work, but are often more difficult to measure, while bulk density $\rho$, and now thermal diffusivity $\alpha$, can be found more readily. Thus, if either the Cp or the K of a material could be determined by experiment, the other property could be calculated.

In theory, one can determine the heat delivered to a sample (Q, in joules) by an energy pulse then measure the increase in the sample's absolute temperature ($\Delta$T). Assuming adiabatic conditions, specific heat capacity (Cp) can then be computed from the equation Cp=Q/m$\Delta$T, where m is the mass of the sample in kilograms. In practice, the heat actually absorbed by a sample cannot be determined with any degree of certainty. It is therefore necessary to use a less direct method of determining heat capacity.

Limited precision can be achieved by testing a sample of known heat capacity, then a sample of unknown heat capacity. If the heat loss for both samples is the same and the energy pulse source does not vary between the tests, the ratio of the maximum temperature increases of the two samples will be equal to the ratio of their respective heat capacities. The above assumptions, however, are a serious limitation on the accuracy of the process. Inaccuracies stem mainly from the fact that there is an appreciable time interval in between measurements because each sample is separately heated to the test temperature, allowed to equilibrate at that temperature, then tested. When there is a long period of time between measurements, it is extremely difficult to provide an energy pulse that is the same and measure the small temperature increases that are due to that energy pulse above the large background noise signals emitted by the furnace environment. As a result, current techniques usually have a scatter of data of about ±10%

SUMMARY OF THE INVENTION

We have invented an instrument for determining certain thermophysical properties of solid samples without measuring or determining the energy absorbed by a sample. In our instrument, a light source is placed at one focus of an elliptical mirror. At the other focus is placed a beam guide that conducts light from the light source into a furnace where it heats samples. At least two samples are heated to the testing temperature at the same time in the furnace, thereby assuring that they are at the same test temperature and eliminating the time required to heat each sample to that temperature by itself A simple light source provides the energy pulse and the light is concentrated by the elliptical mirror before it enters the beam guide. The instrument can hold both diffusivity samples and expansivity samples in the same environment, so that both diffusivity and in-situ density determinations derived from expansivity measurements can be made on the same sample material at the same time.

DESCRIPTION OF THE PREFERRED EMBODIMENTS

Figure 1:
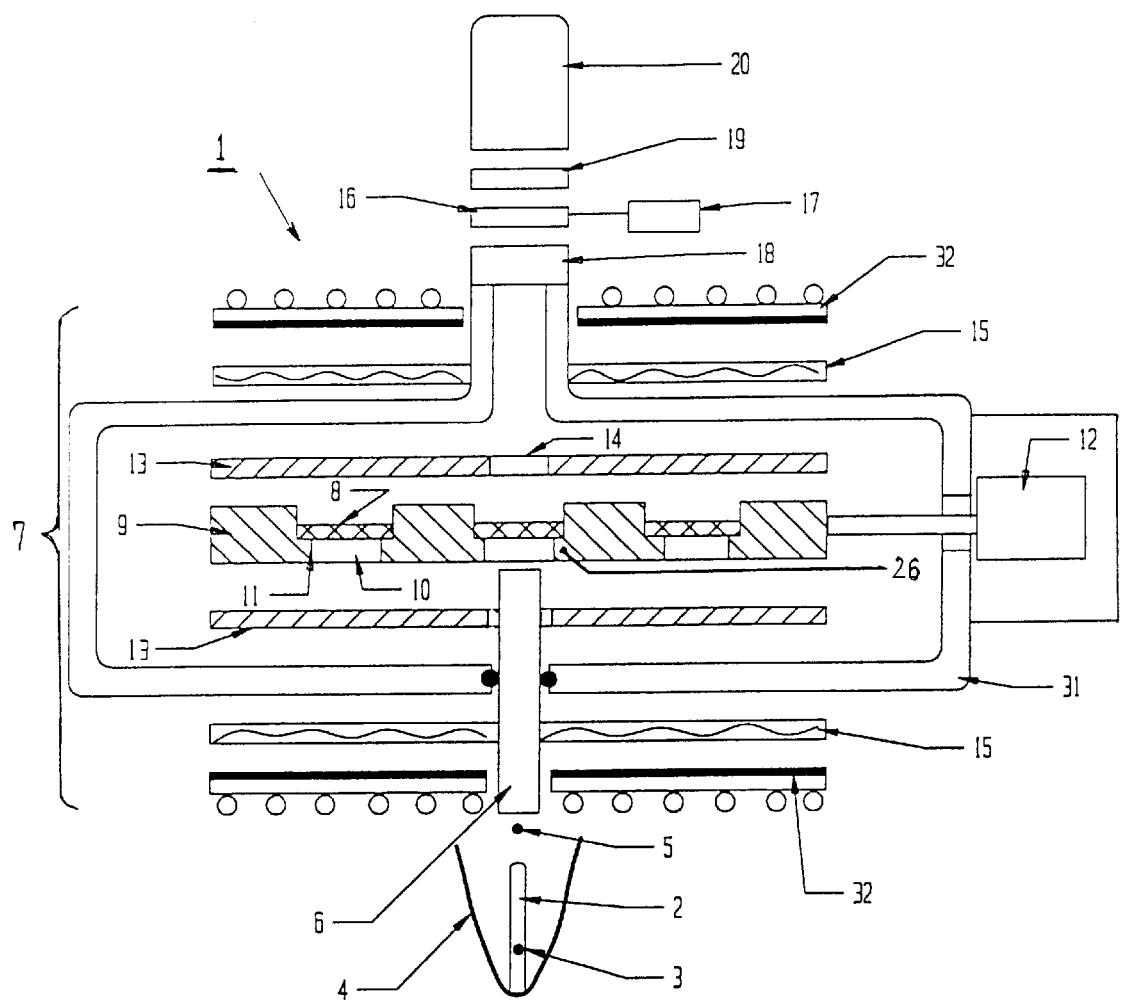
FIG. 1 is a side view in section of a certain presently preferred embodiment of the instrument of this invention.

In FIG. 1, an instrument 1 according to this invention has a light source 2 placed at the focus 3 of elliptical mirror 4 that is closest to elliptical mirror 4. Elliptical mirror 4 has the shape of a portion (preferably about ⅓ to about ½) of an ellipse rotated about its longitudinal axis. Light from light source 2 is reflected by elliptical mirror 4 to its other focus 5 where it enters beam guide 6, which conducts light from light source 2 into furnace 7. The light leaves the other end of beam guide 6 and is absorbed by the front surface of a diffusivity sample 8 held by sample holder 9. For holding samples 8, sample holder 9 is provided with numerous apertures 10 which pass completely through sample holder 9. Each aperture 10 has a rim 11 on which a sample 8 rests. An indexing mechanism 12 moves sample holder 9 so as to place a sample 8 in the path of the light for testing. A susceptor 13 surrounds sample holder 9 to absorb and re-emit infrared heat more uniformly. Susceptor 13 is provided with apertures 14 above and below the sample 8 being tested. (Susceptor 13 can be eliminated if sample holder 9 is made of a highly infrared absorbent material, such as silicon carbide or graphite.) Thermocouples 26 measure the temperature of sample holder 9 in the vicinity of each sample 8. An infrared heat source 15 heats susceptor 13, which in turn heats samples holder 9 and sample 8. Lenses 16 controlled by actuators 17 focus light emitted by the sample being tested and infrared window 18 permits the passage of at least the infrared portion of that light to bandpass filter 19. Bandpass filter 19 permits light of only a narrow range of infrared wavelengths to pass to infrared detector 20, which produces a signal proportional to the temperature of the sample 8 being tested.

Figure 2:
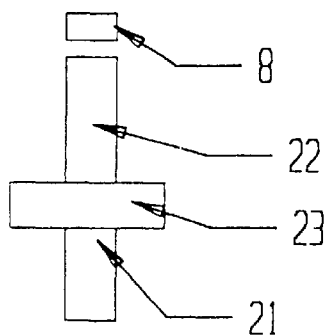
FIG. 2 is a side view in section showing an alternative embodiment of a portion of the structure shown in FIG. 1.

Referring now to FIG. 2, beam guide 6 has been divided into two portions 21 and 22 and beam entry window 23 has been placed between the two portions. Light carried by portion 21 crosses beam entry window 23 and is carried by portion 22 to a sample 8. This embodiment can be used when it is more convenient to seal a window to the furnace than to seal the beam guide to the furnace.

Figure 3A:
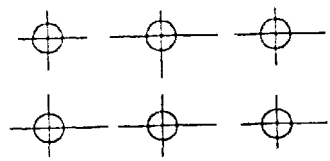
FIGS. 3*a* to 3*f* are plan views showing six different sample indexing configurations.
Figure 3B:
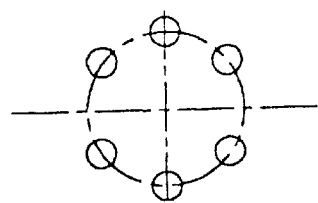
Figure 3C:
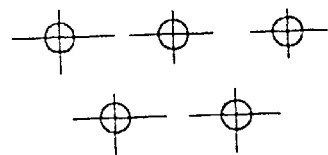
Figure 3D:
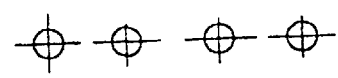
Figure 3E:
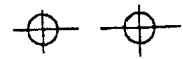
Figure 3F:
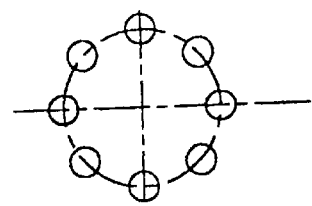

FIGS. 3a to 3f show various sample configurations. The single row linear configuration, FIG. 3d, and the circular configuration, FIG. 3f, are preferred because it is easier to implement indexing and movement for those configurations.

Figure 4:
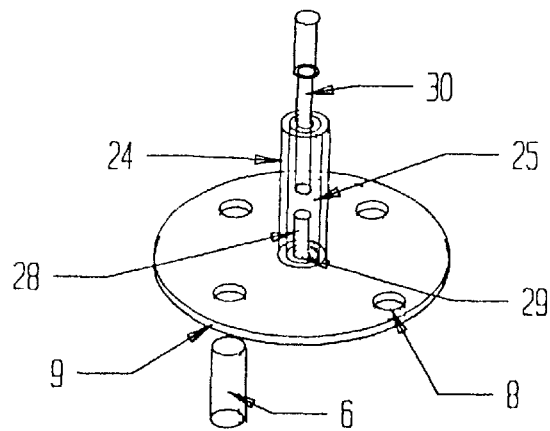
FIG. 4 is an isometric view showing a certain presently preferred indexing system for the instrument of this invention.

In FIG. 4, diffusivity samples 8 are held in a circular configuration in sample holder 9, which is rotated about stem 24. Sleeve 25, inside stem 24, remains stationary.

Figure 5:
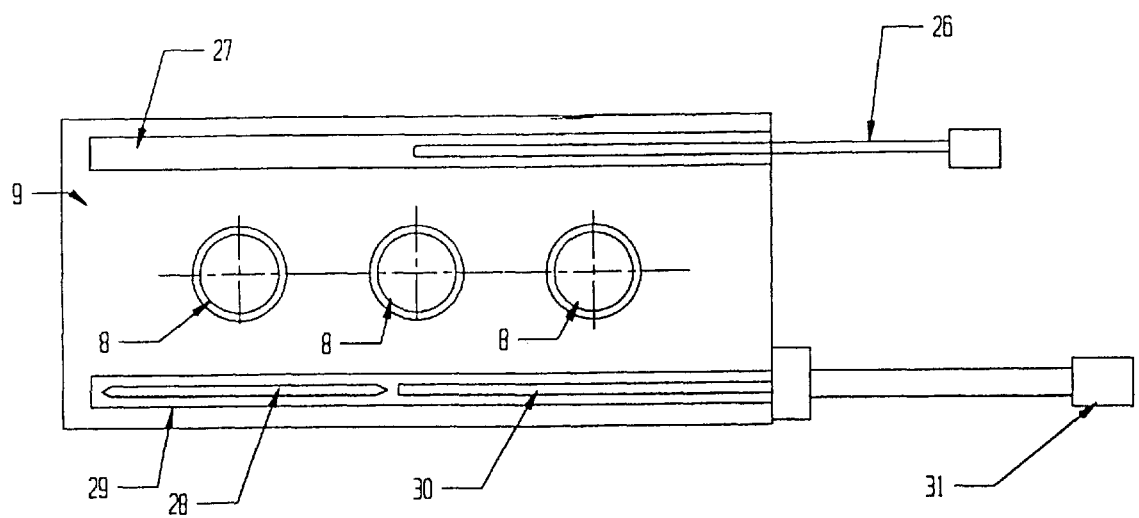
FIG. 5 is a plan view showing an alternative certain presently preferred indexing system for the instrument of this invention.

In FIG. 5, thermocouples 26 are placed in wells 27 on either side of each diffusivity samples 8. An expansivity sample 28 has been placed in a bore 29 in sample holder 9 in contact with the end of bore 29 and push rod 30. Displacement transducer 31 produces a signal proportional to changes in the length of expansivity sample 28.

Various types of light sources can be used to provide an energy pulse to the front surface of a sample, such as xenon flash lamps and quartz-halogen lamps; a xenon flash lamp is the preferred light source because it is the most practical. The light source can have any wavelength, but light that is rich in the ultraviolet (UV) range is preferred as it is higher energy. For good results, the light source should have an output sufficient to raise the temperature of the back surface of the diffusivity sample about 1 or 2K°; higher temperature increases may result in greater heat losses and can be affected by detector nonlinearity. The output of the light source is a single pulse, and the precision of the measurements increases with the shortness of the pulse. The pulse is preferably shorter than about $1/200^{th}$ of the half-max time to avoid serious errors; a practical pulse length is about $1/1000^{th}$ to about $1/500^{th}$ of the half-max time. The pulse is preferably rectangular, but pulses from most sources will be Gaussian, which can be mathematically approximated by a trapezoid, a triangle, or other shape. A pulse mapping sensor can be used to determine the shape of the pulse so that proper mathematical corrections can be made for its deviation from rectangular.

Figure 6B:
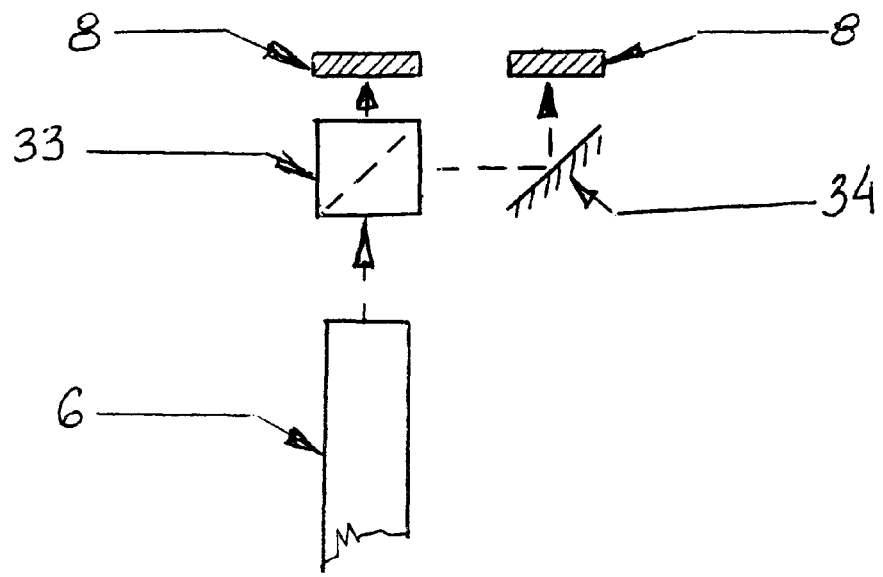
FIG. 6*b* is a plan view showing a split beam guide.
Figure 6A:
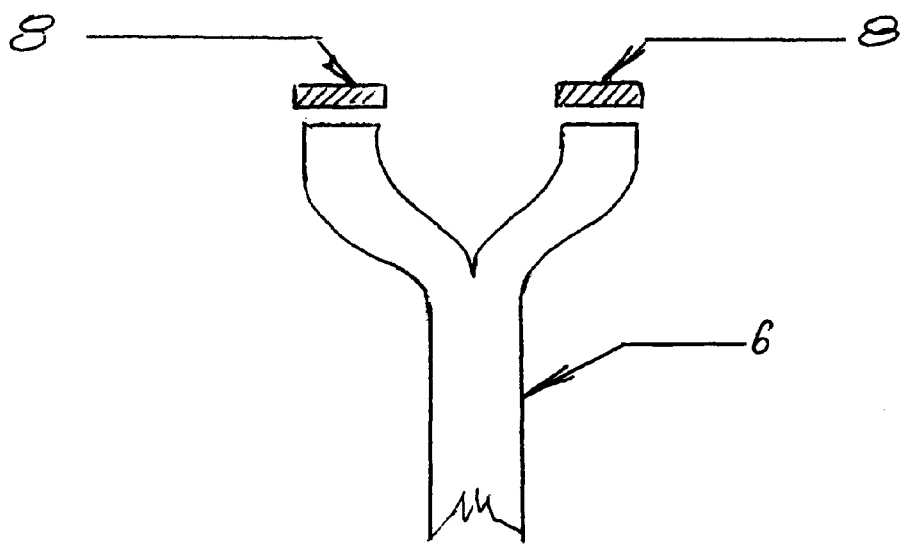
FIG. 6*a* is a plan view showing a beam splitter.

The beam guide conducts the light to the diffusivity sample being tested. The entrance to the beam guide should be positioned within one beam guide diameter of the other focus of the elliptical mirror and is preferably about one-half diameter away from that focus in order to collect the energy over the entire cross section and not just at one point. For best results, the light beam leaving the beam guide should cover the entire diffusivity sample but should not cover much of the sample holder. This typically means that the end of the beam guide should be about 0.01 to about 2 cm away from the diffusivity sample, and preferably about 0.1 to about 0.2 cm away. The beam guide is made of a material that is transparent to the light, such as, depending on the wavelength of the light, polyacrylamide, polyacrylonitrile, glass, quartz, sapphire, silicon carbide, alumina, zirconia, etc. The beam guide may have any cross-sectional shape, but a rod or tube shaped beam guide is preferred as they are easier to work with. Preferably, the cross-section of the beam guide is the same along its length, but, in order to concentrate the light, a beam guide the cross-sectional area of which diminishes from its beginning to its end can be used. The outside surface of the beam guide can be coated with a reflective material to minimize the loss of light. If a tube is used as a beam guide, either or both surfaces can be coated with a reflective material. In another embodiment of this invention, the end of beam guide 6 is split so that the light impinges on two samples 8 at the same time (FIG. 6a) or the light leaving beam guide 6 is passed through a beam splitter 33 and, with the aid of a mirror 35, directed at two samples 8 (FIG. 6b); these embodiments assure that the two samples receive pulses of the same duration, shape, and intensity.

Any type of furnace can be used to heat the samples to the temperature at which they will be tested, such as infrared (IR), resistance heated, high frequency, or microwave; infrared heat is preferred as it is more practical. If the heat source 15 is incandescent, IR-reflective, water-cooled mirrors 32 can be used to concentrate the energy on susceptor 13. The furnace is preferably sealed to keep out environmental influences, such as air movement.

The sample holder is provided with at least two positions for holding diffusivity samples of uniform thickness normal to the path of the light; preferably, it can hold 2 to 24 diffusivity samples. The samples should be held so that front and back surfaces of a sample are exposed and, to minimize heat transfer, the samples should contact the sample holder as little as possible. The sample holder is also preferably provided with at least one bore for holding an expansivity sample. The sample holder can be made of almost any inert material, but materials of high thermal conductivity, such as aluminum, copper, nickel, graphite, alumina, and silicon carbide are preferred as they even out temperature differences between the samples more rapidly; graphite is the most preferred material.

The diffusivity sample can be any material that is a solid during testing or, if not a solid, then contained in a suitable capsule that makes it behave as though it were a solid. The sample is prepared as a thin slice of uniform thickness, preferably in a shape that matches the shape of the light beam. The thinness of the sample is dictated by its thermal diffusivity, but no minimum thinness is required and the instrument can be used to determine the thermal properties of thick diffusivity samples, i.e., samples thicker than 0.5 cm, as well. If the sample material has a coarse structure, such as concrete, sandstone, or firebrick, a thicker sample is preferred to better represent the average characteristics of the bulk material. Before testing, the weight and dimensions of each sample should be determined in order to calculate its density. The expansivity sample can also be of any material that is a solid during testing.

The test temperature of the sample is most conveniently measured using thermocouples. The thermocouples can be placed in wells in the sample holder so that they move with the sample holder, where each thermocouple or set of thermocouples measures the temperature of a particular sample, or they can be fixed and measure the temperature of each sample as it moves into the path of the light beam. Preferably, the thermocouples are fixed to the sample holder as that arrangement is simpler and more precise. Preferably, each thermocouple should be less than 0.5 cm away from the sample the temperature of which it measures.

Sensing a signal proportional to the change in temperature of the back surface of the sample being tested is also necessary. This is most conveniently accomplished using an infrared detector, such as indium antimonide, lead selenide, indium-gallium arsenide, or silicon. Temperature readings should be taken continuously for a time no shorter than 10 seconds or until the temperature of the back surface of the sample has passed its maximum temperature and has substantially declined.

To determine the thermal diffusivity, α, a diffusivity sample is placed in position in the sample holder and moved into the path the light beam will take. The furnace is heated to the temperature at which the test is to be made and is held there until the sample and the sample holder have equilibrated at that temperature. A pulse from the light source is emitted and impinges the front surface of the sample. Changes in the temperature of the opposite surface are taken using the infrared detector. The time (in seconds) for the temperature of the back surface of the sample to reach one-half of its maximum temperature and the thickness of the sample are measured and are used to calculate thermal diffusivity, α, according to the formula $$a = \frac{0.138 d^2}{\pi^2 t_{\frac{1}{2}}}$$

(Alternatively, other formulas can be used that require a different fraction of the maximum temperature and have a different constant, e.g., $\alpha = cd^2/t_x$, where c is a constant and $t_x$ is the time required for the temperature of the sample to reach a fraction, x, of its maximum value.) If desired, the temperature of the furnace can be changed and the procedure repeated to obtain the thermal diffusivity at a different temperature.

To measure the specific heat capacity of a sample, $(Cp)_u$, the sample is placed in the sample holder along with a sample having a similar mass and known specific heat capacity and the furnace is turned on. After the samples and sample holder have equilibrated at the desired temperature, one of the samples is exposed to a light pulse, and then the same test is performed on the other sample. Using the formula $$(Cp)_u = \frac{(Cp)_k \rho_k d_k (T_k M_u)}{\rho_u d_u (T_u M_k)}$$

the specific heat capacity of the sample can be calculated, where $T_k$ is the increase in the temperature of the back surface of the known sample at maximum, one-half max, or some other value, $T_u$ is the increase in the temperature of the back surface of the unknown sample at the same value, $(CP)_k$ is the specific heat capacity of the known sample (J/kgK), $\rho_k$ and $\rho_u$ are the densities of the known and unknown samples, respectively, and $M_k$ and $M_u$ are constants related to the heat loss of the known and unknown samples, respectively, as defined in an article titled, "Specific Heat Measurement in a Multisample Environment with the Laser Flash," by M. A. Thermitus and P. Gaal, *Thermal Conductivity 24/Thermal Expansion 12*, (Lancaster, 1999), Technomic Publishing Co., Inc., pp.1 219–228, herein incorporated by reference. (A variable proportional to the temperature rise of the back surface can be used instead of the temperature of the back surface itself, using corresponding constants.) The thermal conductivity can be calculated using the formula $K = \alpha \rho (Cp)_u$.

To determine the thermal expansivity, $(L-L_o)/L_o$, an expansivity sample of length, $L_o$, is placed in the bore in the sample holder. The furnace is turned on to heat the sample holder and sample to the desired initial temperature, T; room temperature is used as the initial temperature, $T_o$. The length, L, of the sample at T is measured and $(L-L_o)/L_o$ is calculated. The average coefficient of thermal expansion, 1, can then be calculated using the equation $1 = [(L-L_o)/L_o]/[(T-T_o)] = (\Delta L/L_o)/(\Delta T)$. Conversely, a sample of known expansivity and coefficient of thermal expansion can be placed in the bore at $T_o$ and the temperature, T, of the sample holder can be determined from the sample's expansion using that equation. For good results in determining the coefficient of linear thermal expansion of the expansivity sample, it should have a coefficient of thermal expansion significantly larger than the coefficient of thermal expansion of the sample holder; a difference in coefficients of thermal expansion of at least 10 is preferred.

To determine the density, $\rho_T$, of a sample that is isotropic or only slightly anisotropic at a test temperature, T, the mass, M, in kilograms and the perpendicular dimensions, a, b, and c, (cm) of the sample are measured to calculate it volume, $V = a \cdot b \cdot c (cm^3)$. (If the sample is not rectilinear, another formula is used to calculate its volume, V.) The sample is placed in the bore of the sample holder and is equilibrated at the test temperature, T, and l is determined as described hereinabove. The volume of the sample, $V_T$, at T is $V_T = [al(T-T_o)][bl(T-T_o)][cl(T-T_o)] = Vl^3(T-T_o)^3$ and its final density, $\rho_T$, is $M/V_T$.

When the use of thermocouples are not practical for measuring the temperature of a sample, its temperature can be determined by measuring its change in length, ΔL. First, the change in length of a material having a known l is measured to give $\Delta L_{km}$, and its true $\Delta L_{kt}$ is calculated from its known l; the $\Delta L_{sh}$ of the sample holder is calculated using $\Delta L_{sh} = \Delta L_{kt} - \Delta L_{km}$. Then the $\Delta L_{um}$ of an unknown material is measured and true $\Delta L_{ut}$ of the unknown sample is calculated using $\Delta L_{ut} = \Delta L_{sh} + \Delta L_{um}$. From $\Delta L_{ut}$ the temperature of the unknown sample can be determined from the equation $T = (L_{ut} - L_o)/lL_{ut} + T_o$.

To determine the thickness of a diffusivity sample at the test temperature, T, using an expansivity sample of the same material, the two samples are placed in their respective positions as described hereinabove, and the thermal expansivity, $(L-L_o)/L_o$, of the expansivity sample is determined. The thickness, $d_T$, of the diffusivity sample at the test temperature, T, can be calculated using the formula $d_T = d_o [1 + (L-L_o)/L_o]$, where do is the thickness of the diffusivity sample at the initial (ambient) temperature.

The following example further illustrates this invention:

EXAMPLE

Using the methods and apparatus of this invention, the thermal diffusivity, α, of graphite-coated samples of OFHC (oxygen-free, high conductivity copper) and of 99.999% pure aluminum, were tested side-by-side with Poco AXM-5Q, a known reference material. The following table gives the results for OFHC copper:

| Temperature (° C.) | α determined according to this invention (cm²/sec) | Published* Value of α (cm²/sec) | Cp determined according to this invention (Joule/gK) | Published* Value of Cp (Joule/gK) |
|---|---|---|---|---|
| 100 | 1.129 | 1.122 | 0.397 | 0.394 |
| 300 | 1.053 | 1.046 | 0.422 | 0.414 |
| 500 | 0.977 | 0.982 | 0.436 | 0.431 |
| 700 | 0.917 | 0.919 | 0.452 | 0.448 |
| 900 | 0.850 | 0.849 | 0.482 | 0.476 |

The following table gives the results for 9.999% aluminium.

| Temperature (° C.) | α determined according to this invention (cm²/sec) | Published* Value of α (cm²/sec) | Cp determined according to this invention (Joule/gK) | Published* Value of Cp (Joule/gK) |
|---|---|---|---|---|
| 50  | 0.901 | 0.893 | 0.921 | 0.928 |
| 150 | 0.820 | 0.818 | 0.981 | 0.979 |
| 250 | 0.746 | 0.750 | 1.021 | 1.004 |
| 350 | 0.686 | 0.689 | 1.085 | 1.079 |
| 450 | 0.631 | 0.632 | 1.114 | 1.129 |

*White, G. K. and Minges, M. L., 1997, "Thermophysical Properties of Some Key Solids: an Update." *Int. J. Thermophysics*, 18(5): 1269–1327. The above experiments show that the apparatus and methods of this invention permit the derivation of values of specific heat from measurements of thermal diffusivity with a precision of ±1%; makers of commercial equipment for obtaining values of specific heat by testing samples in succession claim a precision of only ±7%.

We claim:

1. An instrument for determining thermophysical properties of a solid sample of uniform thickness comprising
   (A) a furnace;
   (B) an elliptical mirror outside said furnace;
   (C) a light source at the focus of said elliptical mirror that is closest to said elliptical mirror;
   (D) a beam guide having one end at the other focus of said elliptical mirror and the other end inside said furnace;
   (E) a sample holder inside said furnace, capable of holding at least two diffusivity of samples with the front and back surface of a sample exposed when said sample is in the path of light leaving said beam guide;
   (F) an indexing system for moving said sample holder so as to place samples held by said sample holder in the path of light leaving said beam guide, whereby said light impinges on the front surface of a sample; and
   (G) means for quantifying changes in the temperature of the back surface of a sample that is in the path of said light.

2. An instrument according to claim 1 wherein said furnace heats its contents by means of infrared radiation.

3. An instrument according to claim 1 wherein said light source is a flash lamp.

4. An instrument according to claim 3 wherein said flash lamp can emit ultraviolet-rich pulses shorter than $1/200^{th}$ of the half-max time of a sample being tested.

5. An instrument according to claim 1 wherein said beam guide has two parts, one on either side of a window in said furnace.

6. An instrument according to claim 1 wherein said end of said beam guide inside said furnace is split, so that light leaving said beam guide impinges on two samples at the same time.

7. An instrument according to claim 1 wherein a beam splitter splits light leaving said beam guide into two beams which impinge on two samples at the same time.

8. An instrument according to claim 1 wherein said other end of said beam guide is about 0.01 to about 0.2 cm away from a sample being tested.

9. An instrument according to claim 1 wherein said sample holder holds said samples in a circular or linear configuration.

10. An instrument according to claim 1 wherein said sample holder is surrounded by a susceptor having an aperture on each side of a sample that is in the path of said light.

11. An instrument according to claim 1 including means for measuring the temperature of said sample holder in the vicinity of a sample in the path of said light.

12. An instrument according to claim 11 wherein said means for measuring is fixed to said sample holder.

13. An instrument according to claim 11 wherein said means for measuring is at least one thermocouple.

14. An instrument according to claim 1 including a bore in said sample holder for holding an expansivity sample and means for measuring changes in the length of an expansivity sample placed in said bore.

15. A method of determining the average coefficient of thermal expansion, l, of a sample comprising placing a sample of known length, $L_o$, in the bore of the sample holder of an instrument according to claim 14 at an initial temperature, $T_o$, determining its length, L, at a higher temperature, T, and calculating l from the equation $$l=[(L-L_o)/L_o]/[(T-T_o)]=(\Delta L/L_o)/(\Delta T).$$

16. A method of determining the density, $\rho_T$, of a thermal diffusivity sample at a test temperature, T, comprising measuring the volume, V, and mass, M, of said sample, determining its average coefficient of thermal expansion, l, according to the method of claim 15, and calculating its density, $\rho_T$, according to the equation $\rho_T=M/[Vl^3(T-T_o)^3]$.

17. A method of determining the temperature, T, of a sample comprising determining its average coefficient of thermal expansion, l, according to the method of claim 15, and calculating said temperature T according to the equation $T=(L-L_o)/lL+T_o$.

18. A method of measuring the thermal diffusivity, α, of a slice of solid sample having a uniform thickness comprising placing said sample in a sample holder of an instrument according to claim 1, moving said sample into the path of said light, emitting a pulse from said light source, measuring the time required for the temperature of the back surface of said sample to reach a fraction of its maximum value, and calculating α from a formula $\alpha=cd/t_x$, where c is a constant, d is the thickness of the sample, and $t_x$ is the time required for the temperature of the sample to reach a fraction, x, of its maximum temperature.

19. A method of measuring the specific heat capacity, $(Cp)_u$, of a slice of solid first sample having a uniform thickness comprising placing said first sample and a second sample of known specific heat capacity, $(CP)_k$, in the sample holder of an instrument according to claim 1, moving said samples into the path of said light, emitting a pulse from said light source, measuring the time required for the temperature of the back surface of said samples to reach a fraction of their maximum value, and calculating $(Cp)_u$ using the formula $$(Cp)_u = \frac{(Cp)_k \rho_k d_k (T_k M_u)}{\rho_u d_u (T_u M_k)}$$

where $T_k$ is the increase in the temperature of the back surface of the known sample at maximum, one-half max, or some other value, $T_u$ is the increase in the temperature of the back surface of the unknown sample at the same value, $(Cp)_k$ is the specific heat capacity of the known sample, $\rho_k$ and $\rho_u$ are the densities of the known and unknown samples, respectively, and $M_k$ and $M_u$ are constants related to the heat loss of the known and unknown samples, respectively, calculated from the measured time.

20. A method of determining the thermal conductivity, K, of a sample comprising performing the method of claim 19 and calculating K using the formula $K=\alpha\rho(Cp)_u$, where $\alpha$ is the thermal diffusivity of said sample.

21. An instrument according to claim 1 wherein said end of said beam guide is within one beam guide diameter of said other focus.

22. An instrument according to claim 1 wherein said elliptical mirror has the shape of about ⅓ to about ½ of an ellipse rotated about its longitudinal axis.

23. An instrument according to claim 1 wherein light from said beam guide covers an entire sample.

24. An instrument for determining thermophysical properties of a sample of uniform thickness comprising (A) an infrared furnace;

(B) an elliptical mirror outside said furnace;

(C) a flash lamp capable of emitting pulses of ultraviolet-rich light shorter than $\frac{1}{200}^{th}$ of the half-max time of said sample, positioned at the focus of said elliptical mirror that is closest to said elliptical mirror;

(D) a beam guide having one end at the other focus of said elliptical mirror and the other end inside said furnace;

(E) a sample holder inside said furnace, capable of holding 2 to 24 diffusivity samples in a circular or linear configuration, where said sample holder has an aperture therethrough for each diffusivity sample with means for holding each diffusivity sample over or in an aperture, and said sample holder has a bore therein for holding an expansivity sample;

(F) an indexing system for moving said sample holder so as to place diffusivity samples held by said sample holder in the path of light leaving said beam guide, whereby said light impinges on the front surface of a diffusivity sample;

(G) an infrared detector for producing a signal proportional to the temperature of the back surface of a diffusivity sample that is in the path of said light;

(H) means for determining the temperature of a diffusivity sample in the path of said light; and (I) means for producing a signal proportional to a change in the length of an expansivity sample in said bore.

25. An instrument for determining thermophysical properties of a solid sample of uniform thickness comprising (A) an infrared furnace;

(B) an elliptical mirror outside said furnace;

(C) a flash lamp capable of emitting pulses of ultraviolet light having a duration about $\frac{1}{1000}^{th}$ to about $\frac{1}{500}^{th}$ of the half-max time of said sample, positioned at the focus of said elliptical mirror that is closest to said elliptical mirror;

(D) a beam guide having one end about ½ to about 1 diameter away from the other focus of said elliptical mirror and the other end inside said furnace;

(E) a sample holder inside said furnace having 2 to 24 apertures therethrough in a circular or linear configuration with means for holding a diffusivity sample over or in an aperture, and having a bore therein for holding an expansivity sample;

(F) an indexing system for moving said sample holder so as to place samples held by said sample holder in the path of light leaving said beam guide, whereby said light impinges on the front surface of a sample; and (G) an infrared detector for producing a signal proportional to the temperature of the back surface of a sample that is in the path of said light;

(H) thermocouples in said sample holder for measuring the temperature of a sample in the path of said light; and (I) a displacement transducer for producing a signal proportional to a change in the length of an expansivity sample in said bore.

26. An instrument for determining thermophysical properties of a solid sample of uniform thickness comprising (A) an infrared furnace;

(B) a sample holder inside said furnace having 2 to 24 apertures therethrough in a circular or linear configuration with means for holding a diffusivity sample over or in a aperture;

(C) an elliptical mirror outside said furnace;

(D) a flash lamp capable of emitting pulses rich in ultraviolet light of the same duration, shape, and intensity, having a duration about $\frac{1}{1000}^{th}$ to about $\frac{1}{500}^{th}$ of the half-max time of said sample, positioned at the focus of said elliptical mirror that is closest to said elliptical mirror;

(E) a beam guide having one end within one beam diameter from the other focus of said elliptical mirror and the other end inside said furnace, about 0.01 to about 2 cm away from a sample held by said sample holder;

(F) a thermocouple for measuring the temperature of said sample holder in the vicinity of a sample in the path of said light;

(G) an indexing system for moving said sample holder so as to place samples held by said sample holder in the path of light leaving said beam guide, whereby said light impinges on the front surface of a sample in its path; and (H) an infrared detector for producing a signal proportional to the temperature of the back surface of a sample that is in the path of said light.

* * * * *